(12) United States Patent
Perricone et al.

(10) Patent No.: US 11,644,690 B2
(45) Date of Patent: May 9, 2023

(54) LASER PROTECTION EYEWEAR LENSES

(71) Applicant: PerriQuest Defense Research Enterprises, LLC, Meriden, CT (US)

(72) Inventors: Nicholas V. Perricone, Meriden, CT (US); Kristin A. Rauschenbach, Franconia, NH (US)

(73) Assignee: PerriGuest Defense Research Enterprises, LLC, Meriden, CT (US)

( * ) Notice: Subject to any disclaimer, the term of this patent is extended or adjusted under 35 U.S.C. 154(b) by 311 days.

(21) Appl. No.: 17/141,552

(22) Filed: Jan. 5, 2021

(65) Prior Publication Data
US 2021/0271113 A1 Sep. 2, 2021

Related U.S. Application Data

(63) Continuation of application No. 15/411,573, filed on Jan. 20, 2017, now Pat. No. 10,895,761.
(Continued)

(51) Int. Cl.
*G02C 7/10* (2006.01)
*G02B 5/28* (2006.01)
(Continued)

(52) U.S. Cl.
CPC .............. *G02C 7/107* (2013.01); *A61F 9/02* (2013.01); *A61F 9/022* (2013.01); *G02B 1/11* (2013.01);
(Continued)

(58) Field of Classification Search
CPC ............ G02B 1/14; G02B 1/11; G02B 5/288; G02B 1/041; G02C 7/107; G02C 7/104; G02C 2202/16; A61F 9/02; A61F 9/022
(Continued)

(56) References Cited

U.S. PATENT DOCUMENTS 3,519,339 A 7/1970 Hutchinson et al.
5,005,926 A 4/1991 Spielberger
(Continued)

FOREIGN PATENT DOCUMENTS

EP 0540215 A2 5/1993
EP 3 411 734 A2 12/2018
(Continued)

OTHER PUBLICATIONS

"Notification Concerning Transmittal of International Preliminary Report on Patentability (Chapter I of the Patent Cooperation Treaty" For International Patent Application No. PCT/US2015/031694, dated Dec. 1, 2016, 10 Pages, The International Bureau of WIPO, Geneva, Switzerland.
(Continued)

*Primary Examiner* — Collin X Beatty
*Assistant Examiner* — Grant A Gagnon
(74) *Attorney, Agent, or Firm* — Rauschenbach Patent Law Group, PLLC; Kurt Rauschenbach

(57) ABSTRACT

A laser protection eyewear lens includes a lens substrate comprising an embedded wavelength filter having a first filter function, and a multi-layer dielectric filter applied to at least one of an inside and an outside surface of the lens substrate that comprises a second filter function having at least one center wavelength and bandwidth. The first filter function of the embedded wavelength filter and the second filter function of the multilayer dielectric filter produce a combined filter function that attenuates light reflecting off the multi-layer dielectric filter.

20 Claims, 10 Drawing Sheets

Related U.S. Application Data

(60) Provisional application No. 62/289,840, filed on Feb. 1, 2016.

(51) Int. Cl.
    *A61F 9/02* (2006.01)
    *G02B 1/14* (2015.01)
    *G02B 1/11* (2015.01)
    *G02B 1/04* (2006.01)

(52) U.S. Cl.
    CPC ............... *G02B 1/14* (2015.01); *G02B 5/288* (2013.01); *G02C 7/104* (2013.01); *G02B 1/041* (2013.01); *G02C 2202/16* (2013.01)

(58) Field of Classification Search
    USPC ......................................................... 351/159
    See application file for complete search history.

(56) References Cited

U.S. PATENT DOCUMENTS

| | | |
|---|---|---|
| 5,966,240 A | 10/1999 | Lange et al. |
| 7,008,056 B2 | 3/2006 | Hartley et al. |
| 7,202,852 B2 | 4/2007 | Harvie |
| 3,023,195 A1 | 9/2011 | Popov et al. |
| 9,645,414 B2 | 5/2017 | Perricone et al. |
| 10,895,761 B2 | 1/2021 | Perricone et al. |
| 2002/0159155 A1 | 10/2002 | O'Brien |
| 2005/0018131 A1 | 1/2005 | Ishak |
| 2005/0024583 A1 | 2/2005 | Neuberger |
| 2005/0264753 A1 | 12/2005 | Hartley et al. |
| 2010/0110370 A1 | 5/2010 | Krieg-Kowald et al. |
| 2010/0128356 A1 | 5/2010 | Feklistov et al. |
| 2013/0278893 A1 | 10/2013 | Lemay et al. |
| 2015/0092053 A1 | 4/2015 | Sullivan et al. |
| 2017/0219849 A1 | 8/2017 | Perricone et al. |

FOREIGN PATENT DOCUMENTS

| | | |
|---|---|---|
| FR | 2765696 A1 | 1/1999 |
| WO | 2010077411 A1 | 7/2010 |
| WO | 20110130314 A1 | 10/2011 |
| WO | 2017/136165 A2 | 8/2017 |

OTHER PUBLICATIONS

"Notification of Transmittal of the International Search Report and the Written Opinion of the International Searching Authority, or the Declaration" For PCT/US2015/061692, dated Mar. 4, 2016, 12 pages, International Searching Authority/KR, Korean Intellectual Property Office, Daejeon, Republic of Korea.

Dykes, Jim, Psychophysical Test of Contrast Acuity to Aid Operational Effectiveness of Aircrew Laser Eye Protection (LEP), Texas Univ at San Antonio, Fianl rept, Aug. 2005, <Retrieve: https://www.researchgate.net/publication/235176065_PsychophysicaT_Test_of_Contrast_Acuity_to_Aid_Operational_Effectiveness_of_Aircrew_Laser_Eye_Protection_LEP>.

"Notification of Transmittal of the International Search Report and the Written Opinion of The International Searching Authority, or the Declaration" For PCT/US15/031694, Sep. 1, 2015, 13 pages, International Searching Authority/KR, Korean Intellectual Property Office, Daejeon Metropolitan City, Republic of Korea.

Perricone, et al., U.S. Appl. No. 14/946,633, filed Nov. 19, 2015, USPTO.

"Intention to Grant" dated Jul. 28, 2022, in EP Patent Application No. 17747918.5, 5 pages.

"Restriction Requirement" dated Jul. 10, 2019, in U.S. Appl. No. 15/411,573, 7 pages.

"Non-Final Office Action" dated Dec. 27, 2019, in U.S. Appl. No. 15/411,573, 16 pages.

"Notice of Allowance" dated Sep. 17, 2020, in U.S. Appl. No. 15/411,573, 9 pages.

"Notice of Allowance" dated Oct. 28, 2020, in U.S. Appl. No. 15/411,573, 3 pages.

"Search Report" for European Application No. 17747918.5-1122, dated Sep. 12, 2019, 7 pages, European Patent Office, Munich, Germany.

"Notification Concerning Transmittal of International Preliminary Report on Patentability (Chapter 1 of the Patent Cooperation Treaty)" for International Patent Application No. PCT/US2017/014378, dated Aug. 16, 2018, 14 pages, The International Bureau of WIPO, Geneva, Switzerland.

Flight Crew Training Manual, 2002, 389 pages, Airbus.

American National Standard for Safe Use of Lasers, Mar. 16, 2007, 22 pages, Orlando Florida, Laser Institute of America.

Aeronautical Lighting and Other Airport Visual Aids, Aug. 22, 2013, pp. 1-23 , Chapter 2., www.faa.gov/air_traffic/publications/atpubs/aim/aim0201.html/ retrieved Jan. 21, 2014.

Donval, et al., Anti-Dazzling Protection for Air-Force Pilots, Proc. of SPIE, 2002 pp. 83530L-1-83530L-6, vol. 8353, Infrared Technology and Applications XXVIII, SPIE.

Eigenmann, et al., New Developments in Ophtalmic Coatings on Plastic Lenses, p. 9-14, vol. 3175.SPIE.

Friz, et al., Coating Materials, pp. 105-130.

Gvozden, et al., Possibilities of Adjusting the Light Characteristics of Illuminating Devices Based on White and Colored LEDs, J. Opt Technol., Jul. 2010, pp. 442-446, vol. 77, Optical Society of America.

Hou, et al., Ultra-Bright Heads-Up Displays Using a Method of Projected Color Images by Combination of LEDs and Polymer-Dispersed Liquid Crystals, Journal of Display Technology, Mar. 2014, pp. 228-234, vol. 10, No. 3, IEEE.

Rea, A Second Kind of Light, Oct. 2006, pp. 34-39, Denins Guyon, Lighting Research Center, OPN.

Ritt, et al., Research on Laser Protection—An Overview of 20 Years of Activities at Fraunhofer IOSB, Electro-Optical and Infrared Systems: Technology and Applications X, 2013, pp. 88960G-1-88960G-15, vol. 8896, Proc of SPIE.

Aerospace Recommended Practice, pp. 1-14, SAE Subcommittee A-20A/C, Crew Station & Interior Lighting of Committee A-20, Aircraft Lighting.

Seime,et al., Colorimetric Characterization of LCD and DLP Projection Displays, 2003, pp. 349-358, Society for Information Display.

Svensson, et al. Countering Laser Pointer Threats to Road Safety, Jul. 2002, pp. 640207-1-640207-8, vol. 6402 Optics and Photonics for Counterterrorism and Crime Fighting, Proc. of SPIE.

Zukauskas, et al. , Optimization of Solid-State Lamps for Photobiologically Friendly Mesopic Lighting, Dec. 10, 2012, pp. 8423-8432, vol. 51, No. 35, Applied Optics, Optical Society of America.

Wyszecky, et al., Color Science: Concepts and Methods, Quantitative Data and Formulas, 2000, 2nd Edition, pp. 164-169, and 825-830, John Wiley & Sons, Inc. New York.

http://www.faa.gov/about/initiatives/lasers/, 7 pages, retrieved: Mar. 26, 2017.

Search Report for European Patent No. EP15862684, 8 Pages, dated Jun. 8, 2018, European Patent Office, Munich, Germany.

"Notification of Transmittal of the International Search Report and the Written Opinion of the international Searching Authority, or the Declaration" for International Patent Application No. PCT/US2017/014378, dated Jul. 21, 2017, 17 Pages, ISA/KR, Korean Intellectual Property Office, Daejeon, Republic of Korea.

LASER PROTECTION EYEWEAR LENSES

CROSS REFERENCE TO RELATED APPLICATION

This application is a continuation of U.S. patent application Ser. No. 15/411,573, filed on Jan. 20, 2017, entitled "Laser Protection Eyewear Lenses", which claims benefit of U.S. Provisional Patent Application Ser. No. 62/289,840, filed Feb. 1, 2016, entitled "Laser Protection Eyewear Lenses". The entire contents of U.S. patent application Ser. No. 15/411,573, and U.S. Provisional Patent Application Ser. No. 62/289,840 are incorporated herein by reference.

The section headings used herein are for organizational purposes only and should not to be construed as limiting the subject matter described in the present application in any way.

INTRODUCTION

Rapid advances in solid-state laser technology are providing inexpensive commercially available high-power laser devices that are packaged in both hand-held and portable enclosures. Lasers with output powers in the 1-Watt-range have a nominal "ocular hazard distance" that is typically around 100 meters. The term "ocular hazard distance" is the distance at which the maximal permissible eye exposure is reached and is defined by the American National Standards Institute (ANSI). It is possible for someone to flash a hand-held or portable laser device to produce dangerous "laser dazzle" from great distances with these laser devices where the person is difficult or impossible to detect. The term "laser dazzle" is defined herein to mean a laser illumination event experienced by a victim directly, or indirectly, via a reflection, which causes at least some visual distraction or temporary blindness.

Thousands of laser dazzle events have been reported worldwide by pilots and other transportation workers, as well as public safety workers and athletes. Currently, laser protective eyewear is being developed to reduce the light exposure of certain wavelengths to the eye of individuals that experience a laser strike. Several challenges exist to improve the performance of these laser protective eyewear devices. These challenges include increasing the strength of the blocking to certain wavelengths, modifying visual color characteristics, reducing back reflections into the eye from the inside surface of the lens, reducing lens substrate and process cost, simplifying framing processes, reducing weight of the eyewear, reducing complexity of filter production processes, and improving the quality of the coated surfaces.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The skilled person in the art will understand that the drawings, described below, are for illustration purposes only. The drawings are not necessarily to scale, emphasis instead generally being placed upon illustrating principles of the teaching. In the drawings, like reference characters generally refer to like features and structural elements throughout the various figures. The drawings are not intended to limit the scope of the Applicant's teaching in any way.

DESCRIPTION OF VARIOUS EMBODIMENTS

Figure 1:
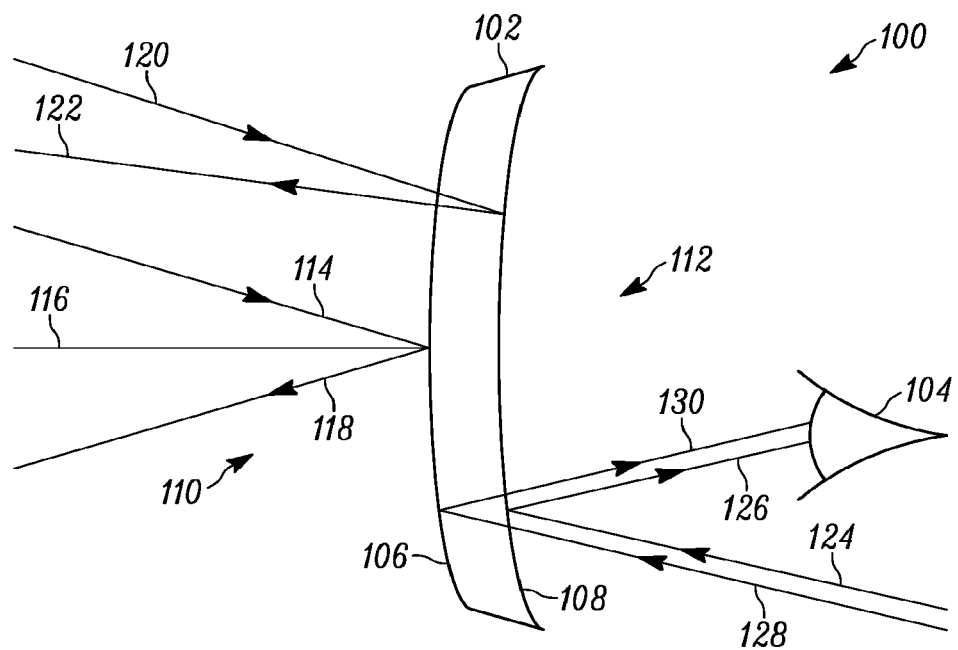
FIG. 1 illustrates a schematic diagram of light paths incident and reflected from the surfaces of the laser protection eyewear lens of the present teaching.

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teachings may be performed in any order and/or simultaneously as long as the teaching remains operable. Furthermore, it should be understood that the apparatus and methods of the present teachings can include any number or all of the described embodiments as long as the teaching remains operable.

The present teaching will now be described in more detail with reference to exemplary embodiments thereof as shown in the accompanying drawings. While the present teachings are described in conjunction with various embodiments and examples, it is not intended that the present teachings be limited to such embodiments. On the contrary, the present teachings encompass various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

The present teaching relates to combining lens substrates comprising integrated spectrally selective wavelength filters with surface-layer filters in order to achieve substantial improvement in laser protective eyewear performance and manufacturability. Many aspects of the present teaching are described in connection with plastic filters that comprise integrated spectrally selective wavelength filters. However, it should be understood that the methods and apparatus of the present teaching apply to any type of lens substrate materials including any type of polymer and plastic lens materials. Also, many aspects of the present teaching are described in connection with integrated absorptive filters. However, it is understood that other types of filters, such as reflective interference filters, can also be integrated into the lens. It is also understood that multiple types of filters, such absorptive and interference filters, can be integrated into the same lens.

Also, many aspects of the present teaching are described in connection with multilayer dielectric interference-type filters. However, it should also be understood that the methods and apparatus of the present teaching apply to any type surface layer filter that is applied to the outside of the lenses. Furthermore, in various embodiments, the surface layer filters can be applied to one or both sides of the lenses. One feature of applying surface layer filters to both sides of a lens substrate is that such filter structures can have reduced variations in effective thin film thickness that are caused by compressive and tensile forces in the filter structures.

Glass lenses with visible color filters, such as those offered by SCHOTT Corporation, are well known. Color filters are typically imparted into glass with various metals. The metals can be incorporated into the glass melt, or can be layered at the surface as metal oxides. Producing color filters in glass substrates is generally more expensive than producing color filters in plastic. For eyewear, color filtering in glass is most typically providing a neutral grey or brown color for sun shading. Specialty applications, such as precision eyewear for target shooting, are known to use glass substrates with various colors of filters, the color being chosen to improve visual acuity and/or concentration.

Color filters are typically imparted into plastic with absorptive dyes. The term plastic, as used herein, is meant to be broadly construed to include any type of polymer including conventional plastics, polycarbonate, high refractive index plastics, and high visual acuity plastics. Many of the dyes are the same dyes that are commonly used in the textile industry. The dyes penetrate deep into the surface of the plastic during manufacturing. These dyes can be used to form almost any type of color filter and the different color possibilities from these dies are virtually unlimited. Some aspects of the present teaching are described in connection with plastic dye based color filters. However, it should be understood that the present teaching is not limited to applications including plastic dye-based color filters.

In one aspect of the present teaching, plastic lens substrates with integrated absorptive spectrally selective wavelength filters are used. Plastic substrates have many desirable features and are widely used today in various types of eyewear. Plastic lenses are desirable for use in laser protection eyewear. For example, plastic lens substrates are relatively light in weight and have good thermal and mechanical properties including exceptional resistance to shatter resistance. In addition, many plastic lenses meet ballistic safety standards, are relatively low cost, and are light in weight. Furthermore, plastic lens substrates are available with low built-in mechanical stress and high temperature tolerance.

Also, in one aspect of the present teaching, multilayer dielectric filters are used. Multilayer dielectric filters are also desirable filters for use in laser protection eyewear because they can be constructed to reflect very narrow wavelength spectrum, while maintaining high transmission of the remaining wavelength spectrum. This results in high visible light transmission over a broad spectrum so the user can still experience good color discrimination. However, laser protection eyewear using dielectric multilayer filters has the disadvantage that it can cause light emanating from behind the lens to be reflected into the user's eye. The light that reaches the eye from a source behind the lens is so-called "back-reflected light".

The combination of a lens substrate comprising at least one integrated spectrally selective wavelength filter with at least one surface-layer filter according to the present teaching has many unique features. In particular, one feature is that the integrated spectrally selective wavelength filter in the lens substrate can be used to reduce back reflections that are produced by multilayer dielectrics interference-type filters formed on one or both sides of the lens. These back reflections reflect into the user's eye and can be distracting in some lighting conditions.

FIG. 1 illustrates the schematic diagram 100 of light paths incident and reflected from the surfaces of the laser protection eyewear lens of the present teaching. A lens 102 is situated in front of a user's eye 104. The lens has an outside surface 106 and an inside surface 108. Light may be incident on the lens from both the front side 110 and the back side 112 of the lens.

Laser protection eyewear lenses with multilayer dielectric filters of the prior art reject laser wavelengths by reflecting those wavelengths away from the surface of the lens, toward the laser source. As is well known, the reflected light path is governed by the electromagnetic reflection rule that states incident light 114 reflects off a reflective surface at an angle equal and opposite of the incident angle as measured from normal 116 to the surface of the reflective surface. In the geometry illustrated in FIG. 1, the incident laser light originates from the front side 110 of the lens 102. If the multilayer dielectric that reflects light with the wavelengths of the incident laser light is positioned on the outside surface 106 of the lens, the light coming from the front of the lens reflects directly from the outside surface layer, and does not enter the lens substrate. This is shown in FIG. 1 with incident light 114 and reflected light 118. If the multilayer dielectric filter that reflects light with the wavelengths of the incident laser light is positioned on the inside surface 108 of the lens, the laser light passes through the substrate and is reflected from the multilayer dielectric back through the substrate and back toward the laser source. This is shown in FIG. 1 with incident light 120 and reflected light 122. The reflection from the multilayer dielectric filters results in a low transmission of those wavelengths through the lens 102, and thereby reduces the amount of laser light that enters the eye 104.

A consequence of the fact that the laser light is reflected away from the surface of the lens is that light with wavelengths falling within the high-reflectance spectral region of the multilayer dielectric filter will also be reflected when incident from the backside 112 of the lens. In this scenario, the wavelengths of light that are reflected from the filter on the inside surface 108 of the lens reflect directly off the inside surface. This is shown in FIG. 1 with incident light 124 and reflected light 126. Those wavelengths of light that are reflected from the filter on the outside surface of the lens pass through the substrate, are reflected off the outside surface, pass through the substrate again, and then continue back toward the user. This is shown in FIG. 1 with incident light 128 and reflected light 130.

The back reflected light is relatively small in most lighting conditions because the light that originates from the backside 112 of the lens in the narrow spectral region reflected by multilayer dielectric filters usually has relatively low intensity. However, even low levels of back reflected light are undesirable to a user especially in situations required for high visual acuity like landing an aircraft. Furthermore, this back-reflected light has a particular color that is perceived by the user which depends on the wavelength of the source light and the particular filter. Thus, one aspect of the present teaching is to provide a laser protective eyewear lens with filtering that reduces the strength of the back-reflected light.

Another aspect of the present teaching is to provide a laser protective eyewear lens with filtering that provides back reflected light with a desirable color spectrum. For example, a desirable color spectrum may be a color spectrum that is chosen to minimize distraction. A desirable color spectrum may also be chosen to present a pleasant hue to the user. A hue is an attribute of a perceived color spectrum for which it is discernable as red, green, blue-green, etc. Hue is independent of intensity. For example, deep blue colors as well as violet hues are known to be less distracting than hues such as red or orange.

In one embodiment of the present teaching, absorptive filters are embedded into the lenses to reduce back reflections. The embedded absorptive filters can also be used to provide part of the overall filter function. Many types of absorptive filters can be integrated into plastic lenses to filter various wavelengths or equivalently various colors. In these filters, light in certain frequency bands or color ranges is partially or totally absorbed in the lens material. In some embodiments, the absorptive filter characteristics are modified by embedding different absorptive dye materials into the plastic. For example, by selecting the proper absorptive dye, notch filters can be constructed that attenuate wavelengths in, for example, the red, green, and blue regions of the electromagnetic spectrum. Absorptive dyes can also be used to provide edge filter profiles. These edge filters can provide a high level of absorption in a range of wavelengths above and/or below a certain wavelength.

Dye-based absorptive filters are commonly used in eyewear to provide ultraviolet (UV) blocking. In addition, dye-based absorptive filters are commonly used in eyewear to provide various tints, such as grey, brown or green tints that are often used for sun protection, but that are also used for providing a fashion colors, such as blue, rose, pink, lavender, yellow, amber, brown and grey. The absorptive filters according to the present teaching can be achieved using numerous methods known in the art.

In one embodiment of the present teaching, the surface layer filters are achieved by depositing multilayer dielectric films on the lens substrates comprising a substrate-embedded wavelength filter using one of numerous thin film deposition processes. The combination of substrate-embedded wavelength filters and surface layer multilayer dielectric filters creates a combined filter that has numerous desirable features. One such desirable feature is that the combined filter can significantly reduce the number of layers in the multi-layer dielectric surface filter. Another desirable feature is that the combination of substrate filters and surface filters achieves particular combined laser rejection filter characteristics while reducing back reflection from the inside surface of the lens into the user's eye which is caused by the surface filter.

Thus, laser protection eyewear according to various embodiments of the present teaching includes a plurality of absorptive filters that are formed in the lens using various absorptive dyes or other means with one or more surface-layer filters to provide for a variety of protection against harmful laser radiation and to provide desirable visual effects.

Figure 2:
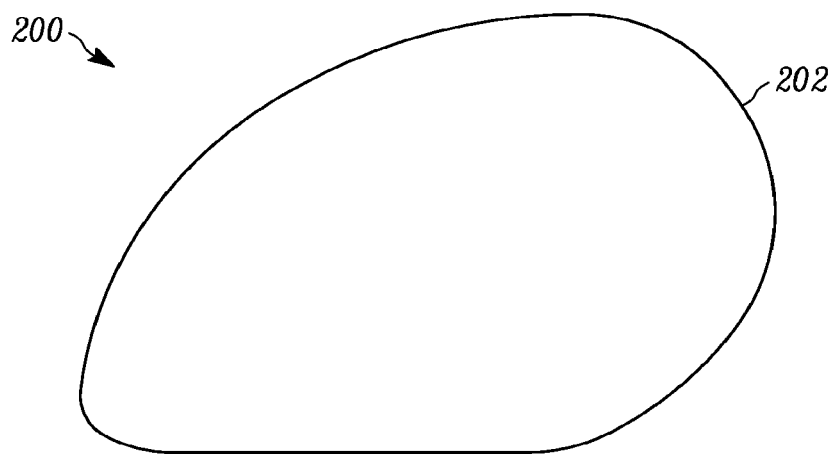
FIG. 2 illustrates a top-view of an embodiment of a laser protection lens of the present teaching.

FIG. 2 illustrates a top-view of an embodiment of a laser protection lens 200 of the present teaching. The perimeter 202 of the lens is shaped to fit within a particular eyewear frame style. Any frame style can be used with lenses according to the present teaching and can include, for example, an aviator, a wrap, a sport, a goggle, a cat-eye, a rimless, a round, or a square style frame. One advantage of using plastic lenses is that the plastic substrate can be cut to form the lens after completion of all processing including the deposition of the surface-layer filters. In contrast, glass lenses need to be cut prior to tempering and surface layer coating.

Figure 3A:
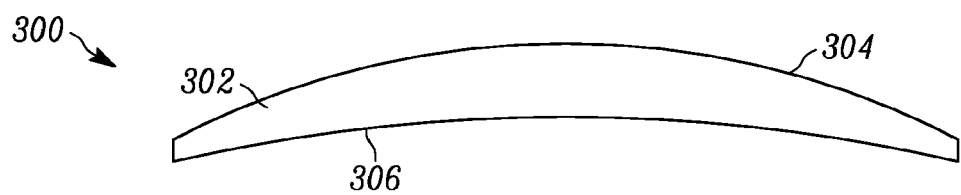
FIG. 3A illustrates a side-view of an embodiment of a laser protection lens of the present teaching.
Figure 3B:
FIG. 3B illustrates a side-view of another embodiment of a laser protection lens of the present teaching.

FIGS. 3A and 3B illustrate a side-view of embodiments of a laser protection lens 300, 320 of the present teaching. The lenses 300, 320 comprise substrates 302, 322 having outside surfaces 304, 324 and inside surfaces 306, 326. The lens 300, 320 may be formed in numerous shapes and can be curved to provide various types of non-corrective and corrective lensing. Corrective lenses are commonly referred to as prescription lenses, as the user will usually obtain a prescription that specifies the curvature of the lens that is appropriate to correct the vision of the user. The lens substrate 302, 322 are typically curved with a so-called "base curve". The base curve affects the shape of the lens on the user's face. A relatively low base curve presents a more flat lens to the user, while relatively higher base curve lens provides more of a wrap around the user's face. Various embodiments of the present teaching use lens substrates with base curves that are between 4 and 10. The lenses can also have different curvatures for the outside surface 304, 324 and for the inside surface 306, 326 as illustrated in the lens 300, 320 of FIGS. 3A and 3B.

The filters of present teaching can be used with so-called plano lenses that do not provide vision correction, as well as with corrective lenses that do provide vision correction. Plano lenses have a curvature that is the same on the inside surfaces 306, 326 and on the outside surfaces 304, 324 of the lens. Corrective lenses have different curvatures of the inside surfaces 306, 326 and outside surfaces 304, 324 that are chosen to provide a particular desired vision correction.

Laser protection eyewear lenses of the present teaching may be produced using various plastic substrates currently used in commercial and/or military-grade eyewear. Plastic materials are an attractive substrate material type for most eyewear lenses because of plastic's relatively high strength-to-weight ratio, relatively high mechanical flexibility, ability to mold into different shapes, relatively high mechanical resilience, relatively high shatter resistance, and relatively low cost. Ophthalmic lenses currently are made from several different types of plastic materials, such as CR39, PMMA, polycarbonates, Trivex®, and high-index plastics. These different plastic materials have significantly different refractive indices. The various plastic materials have refractive indexes that vary from about 1.5 for conventional plastics to about 1.53 for Trivex to about 1.65 for so called high index plastics.

In one specific embodiment, the laser protection lenses of the present teaching are formed of Trivex. Trivex is registered trademark of PPG Industries Ohio, Inc., located at 3800 West 143rd Street Cleveland Ohio 44111. Trivex is a relatively new plastic lens material that is as strong as polycarbonate, but has a higher degree of acuity and inherently lower stress. Trivex is manufactured using a cast molding process and provides significantly lower internal stress and higher visual acuity than polycarbonate and most other plastic-based lenses. Trivex is also lighter weight, and exhibits less internal stress than polycarbonate lens material due to the cast molding manufacturing process. However, Trivex lenses currently are more expensive than conventional polycarbonate and other plastic lenses.

One feature of the laser protection eyewear lenses of the present teaching is the ability to provide laser protection eyewear with protection from ballistic objects. Polycarbonate lenses, in particular, have high strength and high fracture resistance compared with other plastic materials. Polycarbonate lenses are commonly used in ballistic-standard eyewear. Trivex lenses are similarly strong and also can be used when ballistic standards are desired.

Many types of plastic lenses have significant internal stresses. Some internal stresses are introduced during the plastic injection-molding process used to form many types of plastic lenses, such as polycarbonate lenses. Thus, polycarbonate lenses will typically have relatively high internal stress. In general, lens substrates having curved surfaces have natural internal stresses that tend to push the lens flatter, or to tend to pull the lens into a higher curvature structure. These internal stresses can cause small flexure of the lens as it ages or as it is exposed to different environmental conditions, which leads to cracking and "crazing" of the lens material itself or to the applied coatings. Flexure of lenses under stress is especially exacerbated during large temperature changes. Flexure of lenses can be a problem with convention ophthalmic lens that have only a small number of hard coating and/or antireflection coating layers. Flexure is a much more significant problem when a large number of coatings layers are applied, such when a multi-layer dielectric coating is used to construct an interference filter for laser protection eyewear.

Thus, another feature of the laser protection eyewear lenses of the present teaching is the use of plastic substrates that have relatively low stress. Reducing stress in the substrates will reduce "crazing" and adhesion failure events in the spectrally selective surface-layer filters. By using plastic substrate produced with a cast molding process having a low inherent stress, such as Trivex substrates, the laser protection eyewear lenses of the present teaching will have greatly reduced cracking and "crazing" of substrate and surface coating layer. Reducing or eliminating crazing will result in higher performance blocking and better quality visual attributes.

Another feature of the laser protection eyewear lenses of the present teaching is that, in some embodiments, the plastic substrates are formed of a high temperature stability material that is at least somewhat resistant to cracking and "crazing" of the substrate itself and surface coating layers deposited on the substrate. For example, Trivex and similar materials are inherently stable at high temperatures, up to and including the temperatures typically reached in chemical deposition systems during deposition of dielectric coatings. These temperatures can exceed 250 degrees C. during a deposition run, which can exceed six hours. Trivex is 90 percent more resistant to temperature-induced distortion than many conventional plastic substrates, such as polycarbonate substrates. Substrates with relatively high resistance to temperature-induced distortion will not significantly bend, flex, expand, or otherwise change shape during the deposition of multi-layer dielectric coatings using.

Another feature of the laser protection eyewear lenses of the present teaching is that, in many embodiments, the lenses provide a high visual acuity to the user. Certain plastic materials, including Trivex exhibit a high Abbe value. The Abbe value is a metric of the clarity of transparent materials. Theoretically, perfect transparency is defined as 100 on the Abbe value scale. The Abbe value is related to the dispersion of the transparent lens. Dispersion is a variation of the refractive index as a function of wavelength. The reciprocal of the Abbe value is proportional to the dispersion of the material in the region of the spectrum where the human eye is most sensitive. High dispersion tends to spread the focus of the light on the retina because wavelengths of some colors are focused at different positions than other colors owing to the difference in refractive index at different wavelengths. Thus, higher Abbe values and lower dispersion are both metrics of higher visual clarity. Some particular embodiments of the laser protection eyewear lenses of the present teaching use Trivex plastic with a 1.53 refractive index and an Abbe value of between 43 and 45. Other particular embodiments of the laser protection eyewear lenses of the present teaching use polycarbonate plastic with a refractive index of 1.58 and Abbe value between about 28-32.

Another feature of the laser protection eyewear lenses of the present teaching is that, in many embodiments, the lenses are relatively lightweight. Plastic lenses are about half the weight of glass lenses and can provide a similar refractive profile. Polycarbonate is a relatively lightweight plastic material. Trivex is a particularly light plastic material. The so-called high-index plastics are typically heavier per unit volume than Trivex or polycarbonate. However, their higher index plastic material allows the lenses to be thinner. Consequently, the lens weight for a similar refractive profile is similar to or lighter in weight than a Trivex or polycarbonate version making high index plastic materials a good choice for a lightweight substrate.

Lenses according to many embodiments of the present teaching use both a wavelength filter incorporated into the substrate material and a dielectric multilayer filter on a surface of the lens. The resulting lens has a combined filter function that is a linear combination of the filter function of the wavelength filter incorporated into the substrate material and the filter function of the dielectric multilayer filter deposited on the surface of the lens. In the case of a lens with a wavelength filter incorporated into the substrate material and a dielectric multilayer filter on both surfaces of the lens, the resulting lens has a combined filter function that is a linear combination of the filter function of the wavelength filter incorporated into the substrate material, the filter function of the dielectric multilayer filter deposited on the front surface of the lens, and the filter function of the dielectric multilayer filter deposited on the back surface of the lens.

One feature of lens according to the present teaching that have combined filter functions that are a linear combination of the filter function of the wavelength filter incorporated into the substrate material and the filter function of the dielectric multilayer filter deposited on one or both surfaces of the lens is that the wavelength filter incorporated into the substrate material may be absorptive, while the surface filters are reflective. This embodiment allows for a reduction in back-reflected light from the eyewear lens. Referring back to FIG. 1, back-reflected light is incident from the backside 112 of the lens 100. The wavelengths of light that are reflected from the filter on the inside surface 108 of the lens 100 reflect directly off the inside surface as shown by the schematic of the incident light 124 and reflected light 126. The wavelengths of light that are reflected from the filter on the outside surface 106 of the lens 100 pass through the substrate, are reflected off the outside surface 106, pass through the substrate 102 again and continue backward toward the user as shown by the schematic diagram 100 of the incident light 128 and reflected light 130. Thus, the back-reflected light passes twice through the substrate 102, and is impacted by the filter function of the wavelength filter incorporated into the substrate material twice.

In some embodiments, the filter function of the multilayer dielectric filter strongly reflects and/or attenuates laser light of particular wavelengths. These filter functions of the multilayer dielectric filter may be notch filters with particular center wavelengths and bandwidths. These filter functions of the multilayer dielectric filter may also be edge filters with a particular edge wavelength that reflect and/or attenuating either longer or shorter wavelengths than the edge wavelength. The multilayer dielectric filter function may exhibit strong reflection and/or attenuation, as high as 99% or more, at one or more center wavelengths and with one or more bandwidths. The multilayer dielectric filter function may exhibit strong reflection and/or attenuation, as high as 99% or more, at wavelengths longer or shorter than an edge wavelength. For example, the multilayer dielectric filter function may reflect and/or attenuate light in the green region of the spectrum and/or the blue region of the spectrum and/or the red region of the spectrum. The bandwidth of the reflection and/or attenuation may be between 30 nm and 50 nm. One particular example of a filter function that reflects and/or attenuates green light is a filter function with a center wavelength of 532 nm and a bandwidth of between 30 nm and 50 nm. An example of a filter function that reflects and/or attenuates red light is a filter function with a center wavelength of 635 nm and a bandwidth between 30 nm and 50 nm. An example of a filter function that reflects and/or attenuates blue light is a filter function with a center wavelength of 450 nm and a bandwidth between 30 nm and 50 nm. The multilayer dielectric filter function may have one or more notch filters and one or more edge filters. A green notch filter may have a center wavelength of 532 nm, or other green wavelength such as 520 nm, and a bandwidth between 30 nm and 50 nm.

The embedded wavelength filter is designed such that the combined filter function attenuates the light that is strongly reflected and/or attenuated by the multilayer dielectric filter. In some embodiments, the combined filter function attenuates light at the particular center wavelength and bandwidth of the one or more notch filters that are designed to attenuate and/or block incoming laser light. In some embodiments, the combined filter function attenuates light from the filter function of the multilayer dielectric filter comprising edge filters that exhibit a particular edge wavelength and reflect and/or attenuate either longer or shorter wavelengths than the edge wavelength.

In some embodiments, the embedded wavelength filter absorbs light at the particular center wavelength and bandwidth of the one or more notch filters that are designed to attenuate or block incoming laser light. In this way, the combined filter function attenuates light at the particular center wavelength and bandwidth of the one or more notch filters that are designed to attenuate and/or block incoming laser light. In some embodiments, the embedded wavelength filter absorbs light for wavelengths that are either shorter or longer than a particular edge wavelength of the multilayer dielectric filter. In this way, the combined filter function attenuates light from the filter function of the multilayer dielectric filter comprising edge filters that exhibit a particular edge wavelength and reflect and/or attenuating either longer or shorter wavelengths than the edge wavelength. In some embodiments the embedded wavelength filter absorbs light across a bandwidth and center frequency of at least one center wavelength and bandwidth that are reflected and/or attenuated from the multi-layer dielectric filter. In this way, the combined filter function attenuates light reflecting at least one center wavelength and bandwidth off the multi-layer dielectric filter In some embodiments, the wavelengths of light that are reflected from the multilayer dielectric filter on the outside surface of the lens fall within two bands of wavelengths centered around 532 nm and 635 nm. The wavelength filter incorporated into the substrate material is absorptive, and designed to absorb bands of wavelengths that are matched to the two bands of wavelengths centered around 532 nm and 635 nm. In one particular embodiment, the bandwidth of the wavelengths bands is approximately 50 nm. In other embodiments the bandwidth is approximately 30 nm.

Figure 4A:
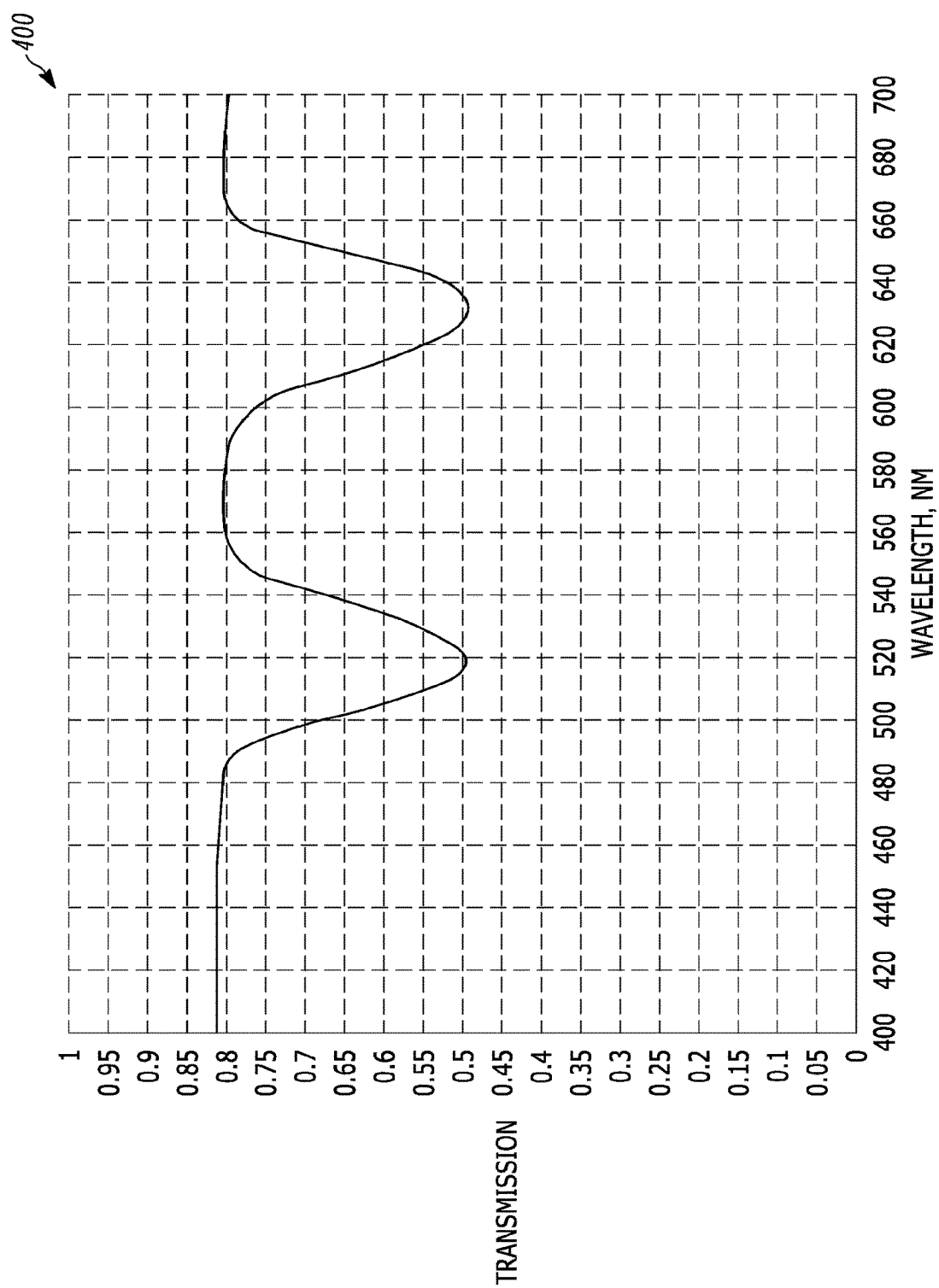
FIG. 4A illustrates a filter function of a filter embedded in a plastic substrate according to the present teaching that absorbs light in two bands of visible wavelengths.

FIG. 4A illustrates a filter function 400 of a filter embedded in a plastic substrate according to the present teaching that absorbs light in two bands of visible wavelengths. The wavelength filter function 400 in the filter embedded in the substrate absorbs two bands of wavelengths centered at 532 nm and 635 nm approximately 50 nm wide to a value of 50% transmission, while the other wavelengths of light have at least 80% transmission or more. In this embodiment, the combined filter function would exhibit nulls at 445 nm, 532 nm and 635 nm wavelengths with strengths of between 95% and 99.9% rejected light.

A configuration with a combined filter function that is a linear combination of the filter function of the wavelength filter incorporated into the substrate material and the filter function of the dielectric multilayer filters deposited on one or both surfaces of the lens greatly reduces the complexity of the dielectric multilayer filters. The reduction in complexity of the dielectric multilayer filter can greatly increase the yield of the dielectric multilayer filter. The reduced complexity of the dielectric multilayer filter results from reducing the filter requirements of the dielectric filter applied to one or both surfaces of the lens. The term "filter requirements" as described herein is not only the absolute rejection of certain wavelengths, but also the steepness of the spectral features produced by the filter.

In some embodiments of the present teaching, the filter function of the wavelength filter incorporated into the substrate material is designed to reduce the steepness of spectral features produced by the filter function of the dielectric multilayer filter deposited on one or both surfaces of the lens, while maintaining a combined filter function with high spectral steepness. Steepness herein refers to the rate of change of the transmission as a function of wavelength. In one example, the combined filter requirement demands that the transmission change from ~80% to ~1% over a wavelength spectral range of 10 nm or less. In another example, the filter requirement for the dielectric multilayer is a transmission change from ~80% to ~1% over a wavelength spectral range of 30 nm or more. In these examples, by adding a wavelength filter in the substrate, the spectral steepness requirement for the dielectric multilayer is significantly reduced. In general, the added filter function from the substrate material serves to reduce the required spectral steepness of the dielectric filter function. The spectral steepness of the filter function of a dielectric multilayer is proportional to the number of layers required to produce the filter function. That is, higher spectral steepness filters require a larger number of layers. Consequently, reducing the spectral steepness requirement of the dielectric multilayer reduces the number of layers in the dielectric multilayer coating, which reduces the complexity and, therefore, the cost of the coating process. Reducing the number of layers also reduces the process time of the coating process, which in turn reduces the temperature of the substrate, and thus generally improves coating quality.

Some embodiments of the filters of present teaching are specifically designed to reduce back reflections into the user's eye that are caused by the dielectric multilayer filter. In these embodiments, the filter function of the wavelength filter incorporated into the substrate material is specifically designed to reduce the rejection of the wavelengths reflected from or transmitted through the dielectric multilayer filter deposited on one or both surfaces of the lens, while maintaining a combined filter function with high rejection for the desired wavelengths.

The strength of the rejection is herein referred to as the value of the filter transmission rejection at particular wavelengths or wavelength ranges. For example, the strength of rejection at a particular wavelength or wavelength range of 99% corresponds to the filter transmission being 1% at the particular wavelength or wavelength range. With no filter in the substrate, this rejection requirement would need to be met entirely by a dielectric multilayer filter alone. By adding a wavelength filter in the substrate, the strength of rejection for the dielectric multilayer can be significantly reduced. For example, the strength of rejection requirement for the dielectric multilayer in this example only needs to be 95% assuming that the wavelength filter incorporated into the substrate material can reject 80% of the particular wavelength or wavelength range. Thus, in general, the added filter function from the substrate material serves to reduce the required strength of rejection of the dielectric filter function for a desired combined filter function. The strength of rejection of the filter function of a dielectric multilayer is proportional to the number of layers required to produce the filter function. In other words, a higher strength of rejection requires a larger number of layers. Consequently, reducing the strength of the rejection requirement of the dielectric multilayer reduces the number of layers in the dielectric multilayer coating. The reduction in the number of layers reduces the cost and the complexity of the coating manufacture process. Reducing the number of layers also reduces the process time of the coating process, which reduces temperature, and thus generally improves coating quality.

Figure 4B:
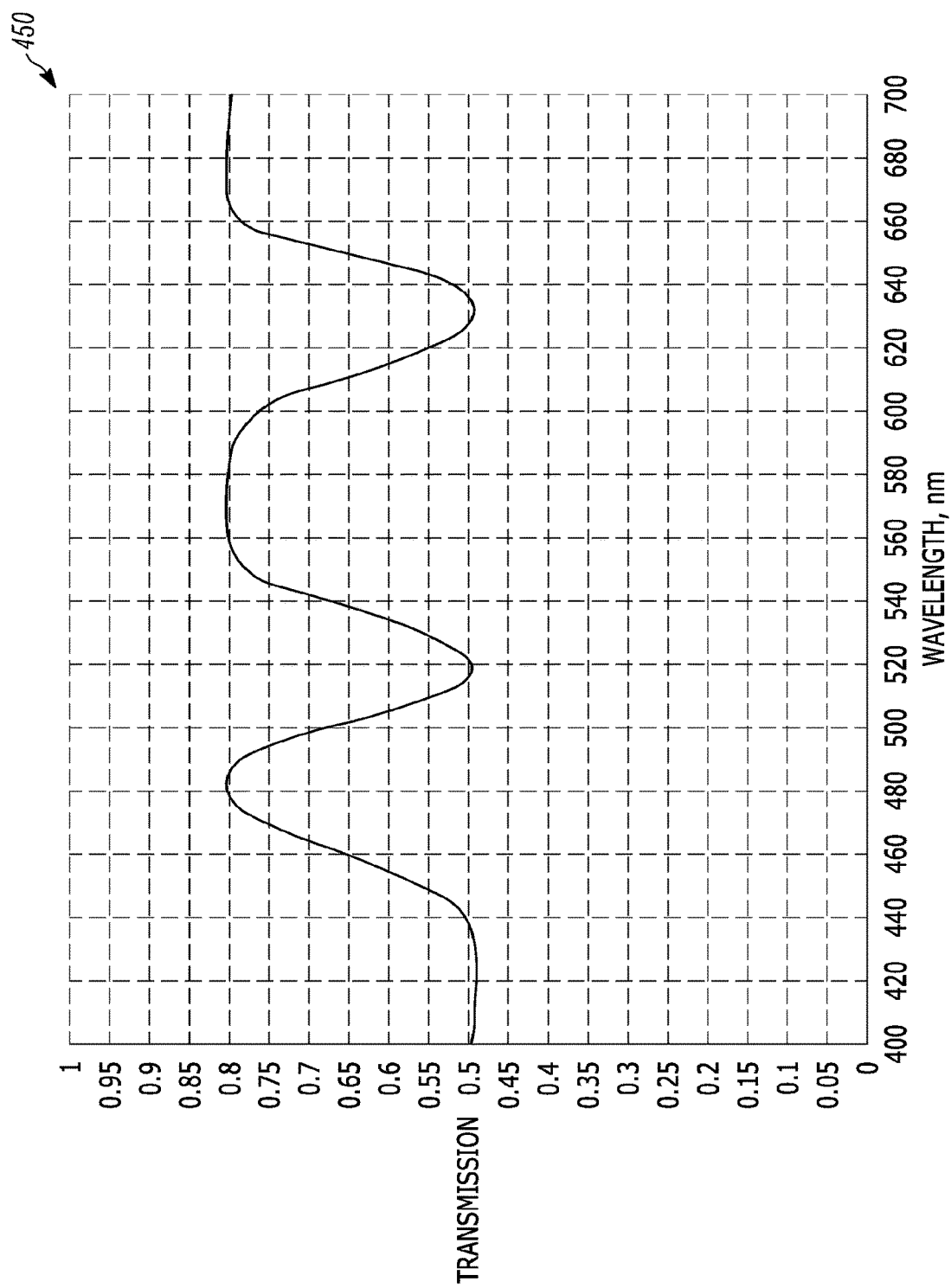
FIG. 4B illustrates a filter function of a filter embedded in a plastic substrate according to the present teaching that absorbs light in two bands of visible wavelengths and at short wavelengths.

FIG. 4B illustrates an embodiment of a wavelength filter function 450 embedded in the plastic substrate that reduces the requirement of the multilayer dielectric filter. This wavelength filter function of the filter embedded in the plastic substrate reduces the strength of rejection requirement at red, green and blue laser wavelengths and also reduces the spectral steepness requirement of the filter function of the dielectric multilayer. The filter embedded in the substrate absorbs 50% of light in two bands of visible wavelengths at 532 nm and at 635 nm, and also at shorter wavelengths less than 445 nm. The multilayer dielectric filter exhibits nulls at 445 nm, 532 nm and 635 nm with strengths of between 85% and 99%. In this embodiment, the combined filter function would exhibit nulls at 445 nm, 532 nm and 635 nm wavelengths with strengths of between 95% and 99.9% rejected light.

In some embodiments, the filter function of the wavelength filter incorporated into the substrate material is chosen to enhance the blocking properties of the surface-layer filter used to block visible laser light. For example, the filter function of the wavelength filter incorporated into the substrate material may be designed to cause reduced transmission in a red, and/or blue and/or green portion of the spectrum. More specifically, the filter function of the wavelength filter incorporated into the substrate material may cause reduced transmission around 532 nm, and/or 635 nm, and/or 445 nm wavelengths.

In some embodiments, the filter function of the wavelength filter incorporated into the substrate material is designed to exhibit an optical edge filter that passes light of wavelengths longer than the blue region of the spectrum, and that blocks light with wavelengths shorter than the blue region of the spectrum. Also, in some embodiments, the filter function of the wavelength filter incorporated into the substrate material is designed to exhibit an optical edge filter function that passes light of wavelengths shorter than the red region of the spectrum and that blocks light with wavelengths longer than the red region of the spectrum. In one specific embodiment, the filter function of the wavelength filter incorporated into the substrate material exhibits an optical edge filter that passes light of wavelengths longer than 450 nm, and also that blocks light with wavelengths shorter than 450 nm. In another specific embodiment, the filter function of the wavelength filter incorporated into the substrate material exhibits an optical edge filter function that passes light of wavelengths shorter than 650 nm and that blocks light with wavelengths longer than 650 nm. In another specific embodiment, the filter function of the wavelength filter incorporated into the substrate material exhibits an optical edge filter function that passes light of wavelengths shorter than 630 nm and that blocks light with wavelengths longer than 630 nm.

In some embodiments of the filter of the present teaching, some spectral features of the combined filter function are provided completely by the wavelength filter in the plastic substrate. For example, a notch or an edge filter that is required to provide laser protection or other visual attribute of the laser protection eyewear may be produced completely within the plastic substrate. This reduces the number of filters that need to be realized in the dielectric multilayer filter, thereby reducing the number of layers.

Figure 5A:
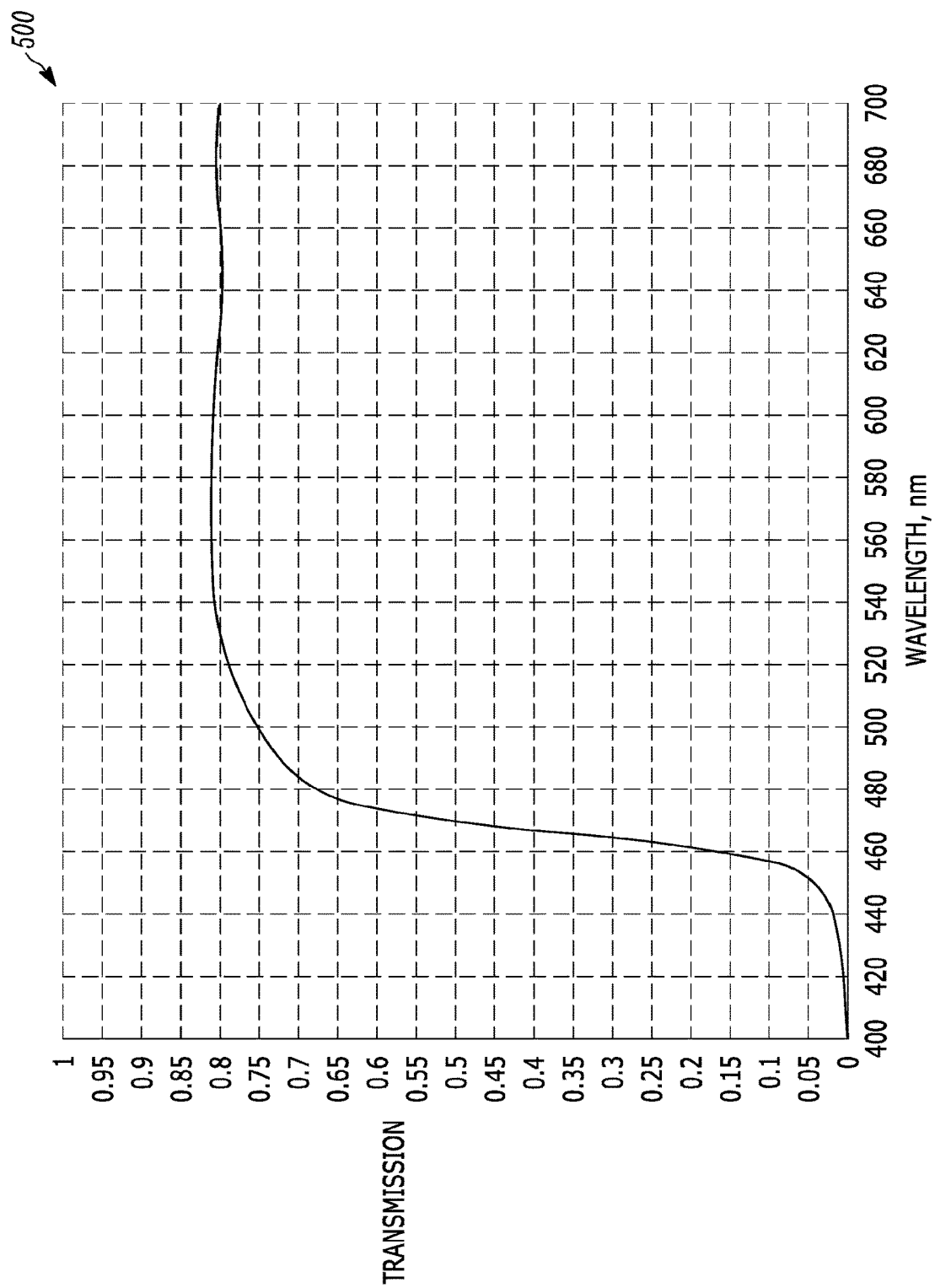
FIG. 5A illustrates blue edge filter function of a filter embedded in a plastic substrate according to the present teaching.

FIGS. 5A-5D illustrate embodiments of wavelength filter functions 500, 510, 520, 530 embedded in the plastic substrate that provide spectral features to a combined filter function. FIG. 5A illustrates a blue edge filter function 500 of a filter embedded in a plastic substrate according to the present teaching. In one embodiment of a combined red, green, blue filter function, the associated multilayer dielectric filter or filters would have a green notch filter and a red notch filter. The combined filter function would exhibit nulls at 445 nm, 532 nm and 635 nm wavelengths with strengths of between 95% and 99.9% rejected light.

Figure 5B:
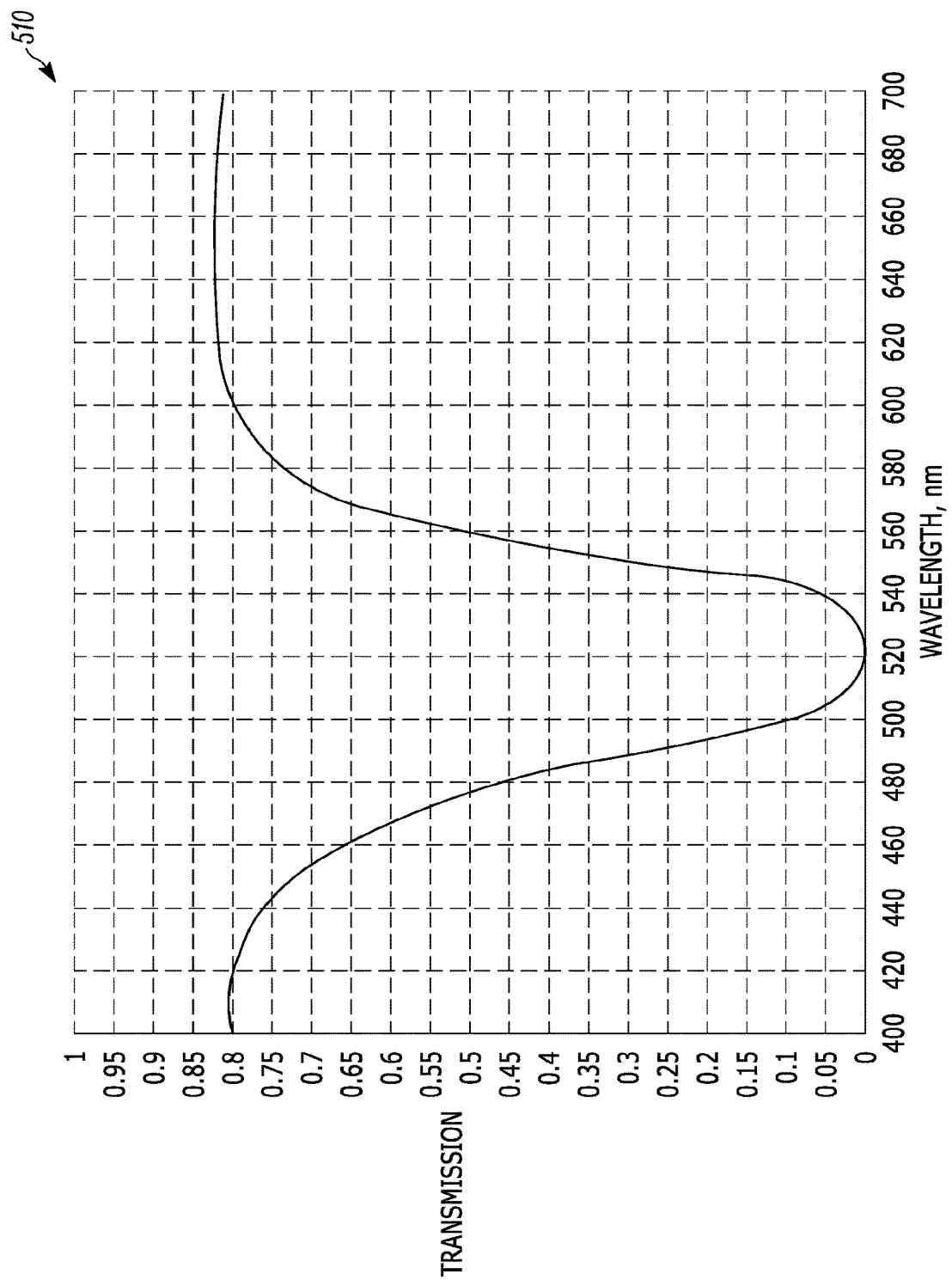
FIG. 5B illustrates a green notch filter function of a filter embedded in a plastic substrate according to the present teaching.

FIG. 5B illustrates a green notch filter function 510 of a filter embedded in a plastic substrate according to the present teaching. In one embodiment of a combined red, green, blue filter function, the associated multilayer dielectric filters would have a blue edge filter and a red notch filter. The combined filter function would exhibit nulls at 445 nm, 532 nm and 635 nm wavelengths with strengths of between 95% and 99.9% rejected light.

Figure 5C:
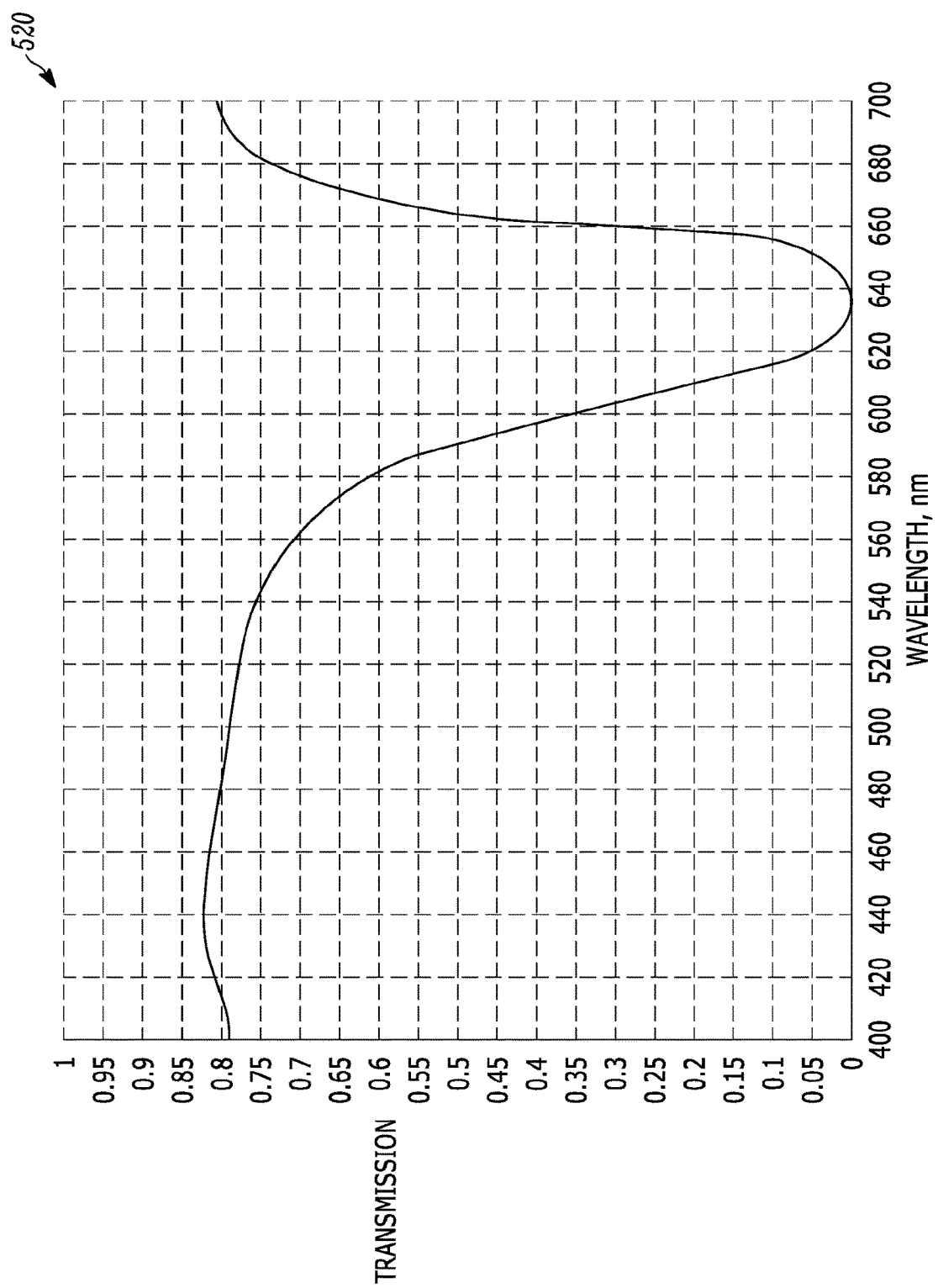
FIG. 5C illustrates a red notch filter function of a filter embedded in a plastic substrate according to the present teaching.

FIG. 5C illustrates a red notch filter function 520 of a filter embedded in a plastic substrate according to the present teaching. In one embodiment of a combined red, green, blue filter function, the associated multilayer dielectric filters would have a blue edge filter and a green notch filter. The combined filter function would exhibit nulls at 445 nm, 532 nm and 635 nm wavelengths with strengths of between 95% and 99.9% rejected light.

Figure 5D:
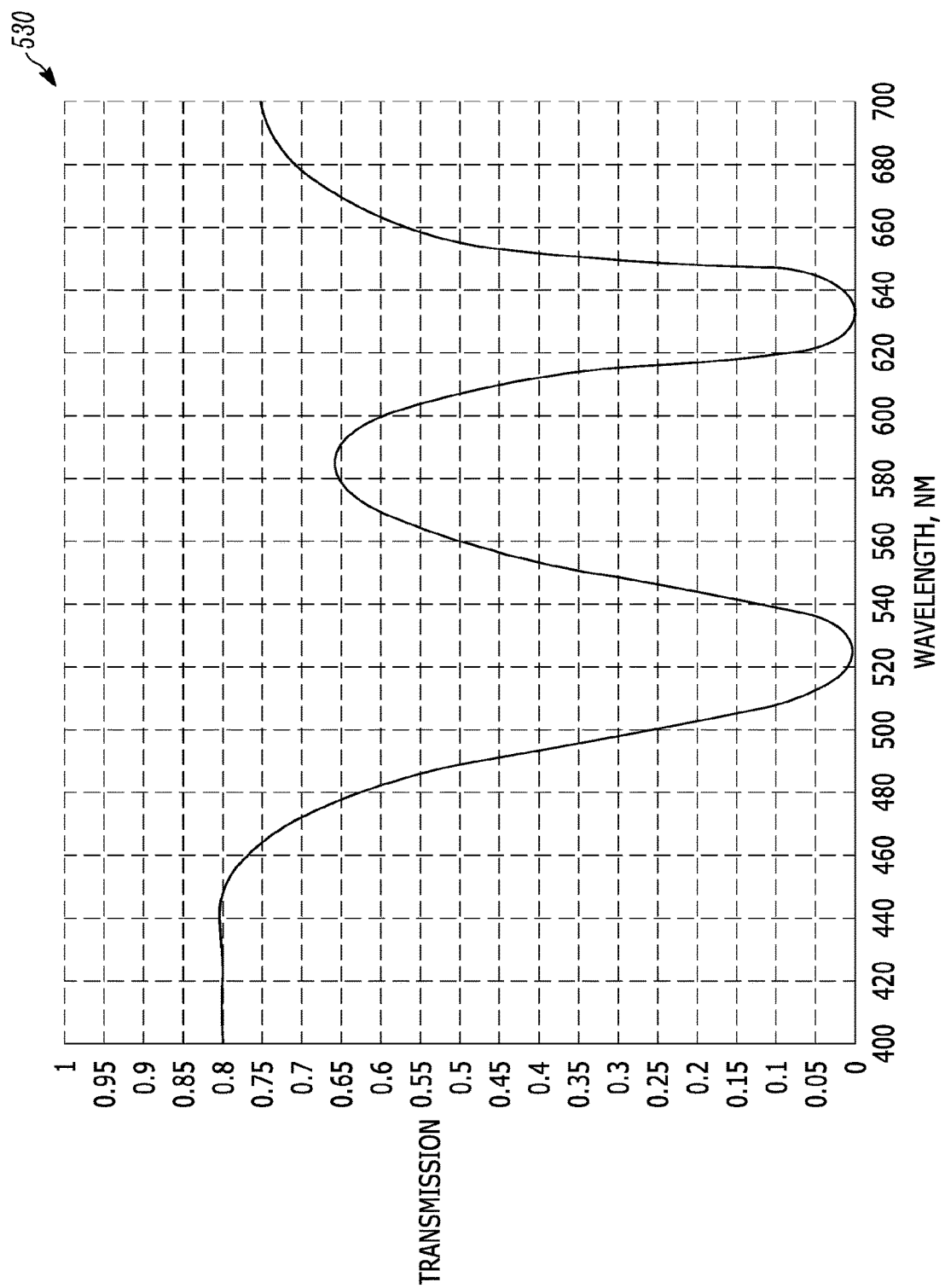
FIG. 5D illustrates a green and red notch filter function of a filter embedded in a plastic substrate of the present teaching.

FIG. 5D illustrates a green and red notch filter function 530 of a filter embedded in a plastic substrate of the present teaching. In one embodiment of a combined red, green, blue filter function, the associated multilayer dielectric filters would have only a blue edge filter. The combined filter function would exhibit nulls at 445 nm, 532 nm and 635 nm wavelengths with strengths of between 95% and 99.9% rejected light.

One feature of the filters of the present teaching is that they can be constructed with a significant reduction in the total number of layers required to form the dielectric multilayer filter for laser protection eyewear lenses. This reduction in the total number of layers makes it easier to achieve a desired filter function by coating the lenses on only one side. Alternatively, multilayer dielectric films can be produced on both sides of the substrate with significantly fewer layers. In some embodiments of laser protection eyewear according to the present teaching including wavelength filters embedded in the plastic substrate, dual surface dielectric multilayer filter can be constructed with 15 or less layers on both surfaces of the lens. In other embodiments of laser protection eyewear according to the present teaching including wavelength filters embedded in the plastic substrate, a single surface dielectric multilayer filter can be constructed with 46 or less layers on only one surface. In yet other embodiments of laser protection eyewear according to the present teaching including wavelength filters embedded in the plastic substrate, a single surface dielectric multilayer filter can be constructed with 20 or less layers on only one surface.

In various embodiments, the filter embedded in the plastic substrate can be designed to have a transmission spectrum that is chosen to achieve particular design goals including one or more of: (1) a reducing in the magnitude of back reflected light; (2) a shift the color of the back reflected light; (3) a reducing the back reflected light emanating from particular colored sources, such as hand-held devices, LED light sources, and signal or notification lights, such as those found in airplane cockpits, motor vehicle passenger compartments, or other transportation vehicle areas where pilots or operators function. In some embodiments, integrated substrate filter reflects back less than 10% of the light from a standard white light source.

Figure 6:
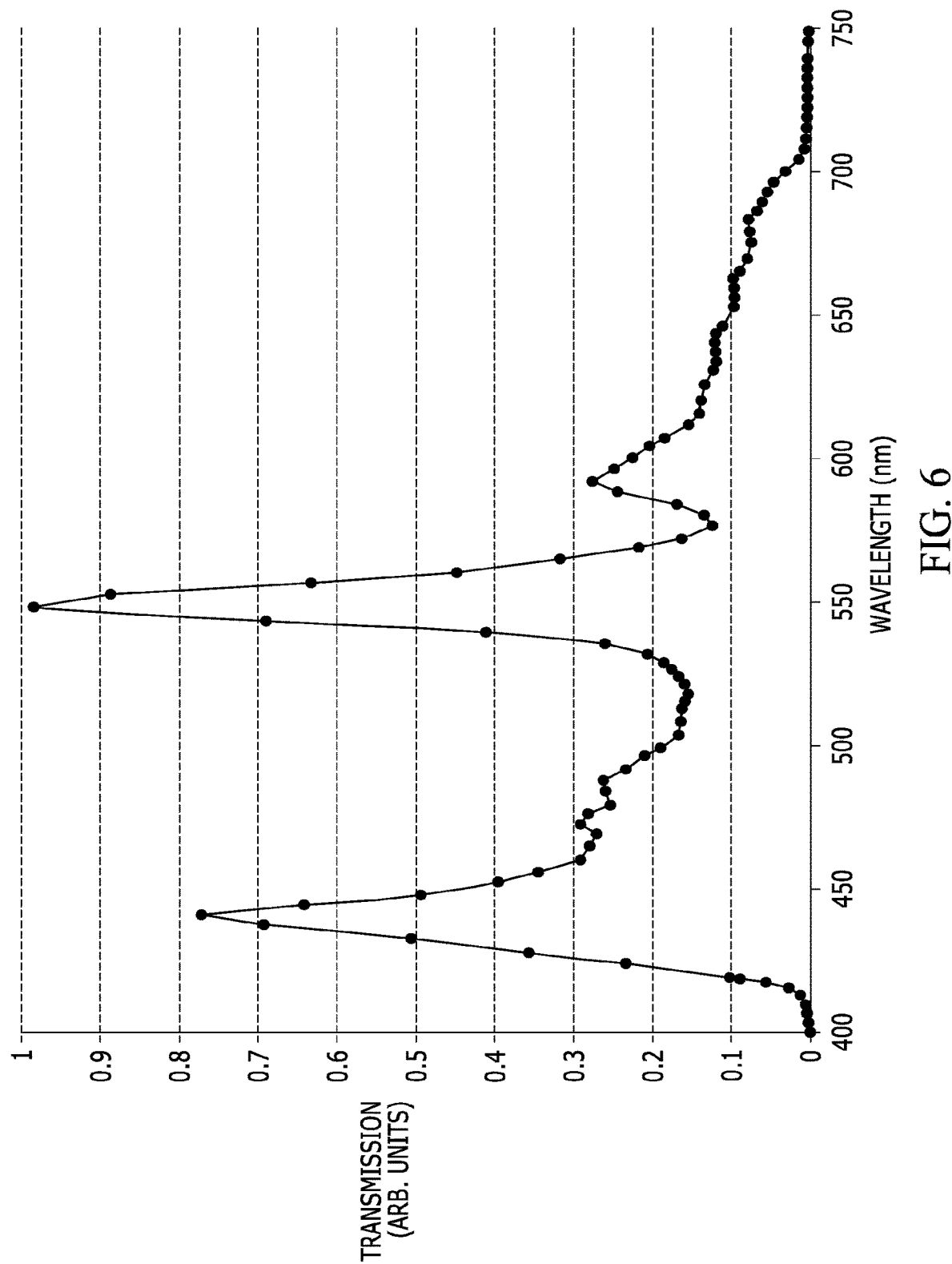
FIG. 6 illustrates a spectrum of illumination from a particular handheld device.

Handheld devices include tablets, smart phones, cell phones, and various other handheld instruments such as global positioning systems. Handheld devices have known spectra that are dependent on the particular technology used for illumination. FIG. 6 illustrates a spectrum of illumination from an Apple IPad that produces white light, which is typical of many handheld devices. In one embodiment of the filter according to the present teaching, the filter function of the embedded substrate filter is chosen to reduce the peaks of the colors emitted from the handheld device by producing a spectrum that has reduced transmission around the wavelengths where the peak transmission occurs and high transmission at the remaining wavelengths.

Figure 7:
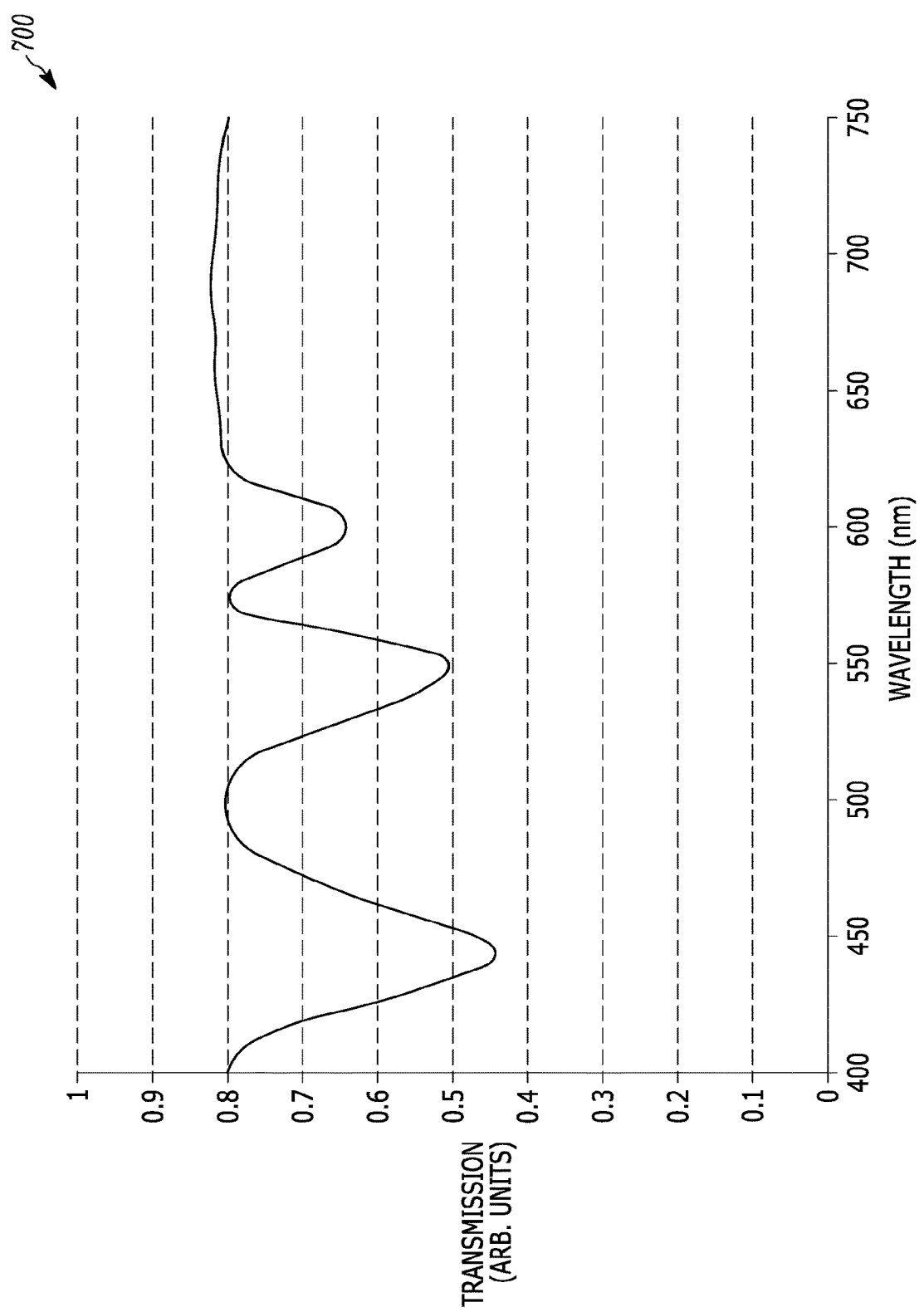
FIG. 7 illustrates a filter function of a filter embedded in a plastic substrate according to the present teaching designed to reduce back reflection from handheld device with the illumination spectrum shown in FIG. 6.

FIG. 7 illustrates a filter function 700 of a filter embedded in a plastic substrate according to the present teaching that is designed to reduce back reflection from handheld device with the illumination spectrum shown in FIG. 6. Note that the filter function 700 is a filter function of an absorptive filter like the filter functions described in connection with FIGS. 4A-B, 5A-4D. In absorptive filters, the light that is not transmitted through the plastic substrate is absorbed in the plastic or other type of substrate material.

One aspect of the present teaching is that it is not required that the filter function of the wavelength filter embedded in the plastic substrate exactly match the shape shown of the spectrum shown in FIG. 7 in order to have good performance. Spectrums of slightly different shapes that generally reduce transmission at parts of the spectrum that exhibit high transmission from the handheld device will also function well. In some embodiments, embedded wavelength filter reflects back less than 5% of the light that enters the backside of the lens from the handheld device. In various embodiments, the filter function of the embedded wavelength filter also blocks certain laser wavelengths.

One skilled in the art will appreciate that the spectra shown in FIGS. 6 and 7 are illustrative of one particular embodiment and do not limit the current teaching. FIG. 6 is illustrative of the peaks in the spectra of the handheld devices. FIG. 7 is illustrative of a spectrum that can reduce the peak intensities of particularly strongly transmitted wavelengths, while passing other wavelengths. As the technology in the handheld devices changes, it is expected that the exact wavelengths of the peaks of the illuminated spectrum emitted from those handheld devices will also change necessitating a change in the embedded substrate filter function.

In various embodiments, the color of the embedded spectral filter in the plastic or glass lens can be chosen to produce a particular "neutral" background color, such as a brown color or a grey color. The color of the plastic or glass substrate material may be chosen to filter out particular parts of the spectrum, such as blue colors in the spectrum that affect night vision and to transmit more red colors that are known to not affect night vision. The color of the plastic or glass substrate may also be chosen to transmit more yellow colors that are known to increase visual acuity and to reduce the amount of short-wavelength light that is known to scatter within the eye which produces glare and other distracting visual effects.

In various embodiment of laser protection eyewear of the present teaching, the plastic or glass substrate includes an embedded filter having a filter function which, when combined with the filter function of the surface-layer filter, provides the desired visual characteristic. The combined filter function is designed to block particular laser light frequencies in the visible, IR and/or UV portions of the spectrum, while passing other wavelengths in the spectrum that allow for high light transmission and good color discrimination. The combined filter function can be specifically designed to provide particular color discrimination or color shifts. For example, the combined filter function can be designed to provide good color discrimination between red, green, and blue. A lens that maintains color discrimination is defined herein as a lens for which a viewer can distinguish particular hues when viewed through the lens. This may include distinguishing a limited set of hues, for example red from green hues, or distinguishing a larger number of hues, such as red, orange, yellow, green, blue, and violet hues. It may also include distinguishing fine grades of hues, such as a reddish-orange hue from a yellow-orange hue.

Color space is used to visually illustrate the eye's ability to separate two distinct colors depends of the hue, saturation and brightness of the observed color. Color space was adopted by the International Commission on Illumination (CIE) in 1976 as a simple-to-compute transformation of the 1931 CIE XYZ color space, but which attempted perceptual uniformity. Adams chromatic valence color space, abbreviation as CIELUV, is an update of the CIE 1964 color space, abbreviated as CIEUVW. The well-known CIELUV formulation provides the color difference between two color stimuli presented in terms of L*, u*, and v*, is given by:

$$\Delta E_{uv}^* = [(\Delta L^*)^2 + (\Delta u^*)^2 + (\Delta v^*)^2]^{1/2}.$$

In general, color difference between two colors should be greater than 40 $\Delta E_{Y_{i'v'}}$ for color the classification stated in the CIEYUV color space; where the CIEYUV color space and is related to the CIELUV space by the transformation: $Y=25L^{*3}$, $u'=u^*$, $v'=\frac{3}{2}v^*$. Thus, a combined filter function must maintain more than 40 $\Delta E_{Y_{i'v'}}$ for all colors that must be discriminated to perform a particular function or identify a particular element.

In one aspect of the present teaching, the combined filter function of an embedded substrate filter and a surface filter operates to produce a particular desired color of back reflected light. For example, in one particular embodiment according to the present teaching, the color of the back reflected light when illuminated with a standard white light source is a deep blue color. In other particular some embodiments, the color of back reflected light is a violet color. In some embodiments, the color of the back reflected light illuminated by IPads and similar handheld devices is a deep blue color. Furthermore, the color of the back-reflected light can be chosen to minimize distraction. The color of the back-reflected light produced by the combined filter function can also be chosen to provide a color associated with the particular market brand of the eyewear. Furthermore, in some embodiments, the color of the back reflected light can be selected specifically to provide a sense of well-being for the eyewear user.

Certain embodiments of the embedded filter and surface filter are designed to provide a combined filter function that provides transmission that favors light that stimulates the l-cones in the eye, while reducing the light that stimulates m-cones and s-cones in the eye, and while also blocking a narrow band of wavelengths around 525-532 nm that is emitted by green lasers. These embodiments of the combined filter function provide an improvement of visual acuity under particular viewing conditions, while providing the desired protection from certain dangerous wavelengths emitted by relatively high power handheld lasers.

One skilled in the art will appreciate that the present teachings are not limited to filters that block visible light. In particular, lenses with a combination of embedded filters and surface layer filters can be designed to have a combined filter function that blocks infrared and/or UV portions of the spectrum. Blocking can be provided for various reasons, in addition to blocking dangerous laser radiation, such as to reduce exposure of the eye to UV from the sun, or to reduce heat effects of infrared radiation.

In some embodiments, the filters of the present teaching also provide the user with desirable eyewear features, such as scratch resistance, UVA/UVB blocking, shatter resistance, anti-static, polarizers, glare reduction, anti-reflection, sun protection for daytime wear, and darkness contrast enhancement for nighttime wear. In various embodiments of the present teaching, these features can be provided by one or both of the embedded substrate filter and/or the surface filter.

EQUIVALENTS

While the applicant's teaching is described in conjunction with various embodiments, it is not intended that the applicant's teaching be limited to such embodiments. On the contrary, the applicant's teaching encompass various alternatives, modifications, and equivalents, as will be appreciated by those of skill in the art, which may be made therein without departing from the spirit and scope of the teaching.

What is claimed is:

1. A laser protection eyewear lens comprising:
   a) a lens substrate comprising an embedded wavelength filter having a first filter function comprising a shape that reduces transmission for at least one wavelength of the spectrum that exhibits high transmission from a handheld device while passing other wavelengths of the spectrum; and
   b) a multi-layer dielectric filter applied to at least one of an inside and an outside surface of the lens substrate, the multilayer dielectric filter comprising a second filter function comprising a notch filter function having at least one center wavelength and bandwidth,
      wherein the first filter function of the embedded wavelength filter and the second filter function of the multilayer dielectric filter produce a combined filter function that rejects incident laser light and reduces back reflection from the handheld device.

2. The laser protection eyewear lens of claim 1 wherein the at least one wavelength of the spectrum that exhibits high transmission from the handheld device comprises a wavelength between 540 nm and 560 nm.

3. The laser protection eyewear lens of claim 1 wherein the at least one wavelength of the spectrum that exhibits high transmission from the handheld device comprises a wavelength between 420 nm and 450 nm.

4. The laser protection eyewear lens of claim 1 wherein the at least one wavelength of the spectrum that exhibits high transmission from the handheld device comprises a wavelength between 590 nm and 600 nm.

5. The laser protection eyewear lens of claim 1 wherein the notch filter function comprises a green center wavelength with a bandwidth between 25 and 55 nm.

6. The laser protection eyewear lens of claim 1 wherein the notch filter function comprises a green center wavelength with a bandwidth between 25 and 55 nm and a blue center wavelength with a bandwidth between 25 and 55 nm.

7. The laser protection eyewear lens of claim 1 wherein the notch filter function comprises a green center wavelength with a bandwidth between 25 and 55 and a red center wavelength with a bandwidth between 25 and 55.

8. The laser protection eyewear lens of claim 1 wherein the notch filter function comprises a green center wavelength with a bandwidth between 25 and 55, a blue center wavelength with a bandwidth between 25 and 55, and a red center wavelength with a bandwidth between 25 and 55.

9. The laser protection eyewear lens of claim 1 wherein the lens substrate is formed of a polymer that is selected from the group consisting of CR39, PMMA, and polycarbonate.

10. The laser protection eyewear lens of claim 1 wherein the lens substrate comprises a glass lens substrate.

11. The laser protection eyewear lens of claim 1 wherein the lens substrate comprises a prescription lens substrate.

12. The laser protection eyewear lens of claim 1 wherein a base curve of the lens substrate is selected from the group consisting of a base 4 curve, a base 6 curve, a base 8 curve, and a base 9 curve.

13. The laser protection eyewear lens of claim 1 wherein the embedded wavelength filter comprises an absorptive filter.

14. The laser protection eyewear lens of claim 1 wherein the embedded wavelength filter comprises a dye-based absorptive filter.

15. The laser protection eyewear lens of claim 1 wherein the embedded wavelength filter comprises an interference filter.

16. The laser protection eyewear lens of claim 1 wherein the embedded wavelength filter attenuates infrared wavelengths.

17. The laser protection eyewear lens of claim 1 wherein the embedded wavelength filter attenuates ultraviolet wavelengths.

18. The laser protection eyewear lens of claim 1 wherein the multilayer dielectric filter is applied to both the inside and the outside surface of the lens substrate.

19. The laser protection eyewear lens of claim 1 wherein the combined filter function produces a combined filtered spectrum that maintains color discrimination of red, green and blue hues.

20. The laser protection eyewear lens of claim 1 wherein the handheld device is selected from a group consisting of tablets, smart phones, cell phones and GPS device.

* * * * *